United States Patent
Alessio

(10) Patent No.: US 9,538,971 B2
(45) Date of Patent: Jan. 10, 2017

(54) SYSTEMS FOR CHARACTERIZING ATHEROSCLEROTIC PLAQUE AND METHODS OF USING SAME

(71) Applicant: University of Washington through its Center for Commercialization, Seattle, WA (US)

(72) Inventor: Adam Alessio, Seattle, WA (US)

(73) Assignee: University of Washington, Seattle, WA (US)

( * ) Notice: Subject to any disclaimer, the term of this patent is extended or adjusted under 35 U.S.C. 154(b) by 52 days.

(21) Appl. No.: 14/313,666

(22) Filed: Jun. 24, 2014

(65) Prior Publication Data

US 2014/0376687 A1    Dec. 25, 2014

Related U.S. Application Data

(60) Provisional application No. 61/838,507, filed on Jun. 24, 2013.

(51) Int. Cl.
*A61B 6/00* (2006.01)
*A61B 6/03* (2006.01)

(52) U.S. Cl.
CPC ............ *A61B 6/504* (2013.01); *A61B 6/032* (2013.01); *A61B 6/4241* (2013.01); *A61B 6/482* (2013.01); *A61B 6/5205* (2013.01); *A61B 6/542* (2013.01)

(58) Field of Classification Search
CPC ..................................................... A61B 6/482
See application file for complete search history.

(56) References Cited

U.S. PATENT DOCUMENTS

| | | | |
|---|---|---|---|
| 7,627,078 B2 | 12/2009 | Hsieh et al. | |
| 7,778,380 B2 | 8/2010 | Altman et al. | |
| 7,983,382 B2 | 7/2011 | Thomsen et al. | |
| 8,055,039 B2 | 11/2011 | Wu et al. | |
| 8,290,232 B2 | 10/2012 | Liu et al. | |
| 8,311,181 B2 | 11/2012 | Thomsen et al. | |
| 2004/0136491 A1* | 7/2004 | Iatrou | A61B 5/02007 378/4 |
| 2011/0141102 A1 | 6/2011 | Skinner et al. | |
| 2012/0087463 A1* | 4/2012 | Greenberg | G01T 7/005 378/5 |

OTHER PUBLICATIONS

E. Falk et al. "Coronary Plaque Disruption" Circulation, vol. 92, No. 3 (Aug. 1, 1995), pp. 657-671.
E. Roessl et al. "K-Edge Imaging in X-Ray Computed Tomography Using Multi-Bin Photon Counting Detectors" Physics in Medicine and Biology, vol. 52 (2007), pp. 4679-4696.
E. Roessl et al. "Preclinical Spectral Computed Tomography of Gold Nano-Particles" Nuclear Instruments and Methods in Physics Research A, vol. 648 (2011), pp. S259-S264.
H. Ding et al. "Image-Based Spectral Distorsion Correction for Photon-Counting X-Ray Detectors" Medical Physics, vol. 39, No. 4 (Apr. 2012), pp. 1864-1976.

(Continued)

*Primary Examiner* — Hoon Song
(74) *Attorney, Agent, or Firm* — Perkins Coie LLP

(57) ABSTRACT

The present technology relates generally to systems for characterizing atherosclerotic plaque, such as a spectral CT system, and methods of using same.

21 Claims, 16 Drawing Sheets
(8 of 16 Drawing Sheet(s) Filed in Color)

(56) References Cited

OTHER PUBLICATIONS

H. Le et al. "Least Squares Parameter Estimation Methods for Material Decomposition with Energy Discriminating Detectors" Medical Physics, vol. 38, No. 1 (Jan. 2011), pp. 245-255.
H. Le et al. "Segmentation and Quantification of Materials with Energy Discriminating Computed Tomography: A Phantom Study" Medical Physics, vol. 38, No. 1 (Jan. 2011), pp. 228-237.
J. Bulte, "Can CT Be Performed for Multicolor Molecular Imaging?" Science to Practice, vol. 256, No. 3 (Sep. 2010), pp. 675-676.
J. Narula, "Who Gets the Heart Attack: Noninvasive Imaging Markers of Plaque Instability" Journal of Nuclear Cardiology, vol. 16, No. 6 (Nov./Dec. 2009), pp. 860-868.
J.P. Schlomka et al. "Experimental Feasibility of Multi-Energy Photon-Counting K-Edge Imaging in Pre-Clinical Computed Tomography" Physics in Medicine and Biology, vol. 53 (Jul. 2008), pp. 4031-4047.
K. Taguchi et al. "Interior Region-of-Interest Recontruction Using a Small, Nearly Piecewise Constant Subregion" Medical Physics, vol. 38, No. 3 (Mar. 2011), pp. 1307-1312.
K. Taguchi et al. "Modeling the Performance of a Photon Counting X-Ray Detector for CT: Energy Response and Pulse Pileup Effects" Medical Physics, vol. 38, No. 2 (Feb. 2011), pp. 1089-1102.
M. Barreto et al. "Potential of Dual-Energy Computed Tomography to Characterize Atherosclerotic Plaque: Ex Vivo Assesment of Human Coronary Arteries in Comparison to Histology" Journal of Cardiovascular Computed Tomography, vol. 2, No. 4 (Jul./Aug. 2008), pp. 234-242.
P. Engler, "Review of Dual-Energy Computed Tomography Techniques" The American Society for Nondestructive Testing, Inc. Materials Evaluation, No. 48 (May 1990) pp. 623-629.
P. Sukovic et al. "Penalized Weighted Least-Squares Image Reconstruction for Dual Energy X-Ray Transmission Tomography" IEEE Transactions on Medical Imaging, vol. 19, No. 11 (Nov. 2000), pp. 1075-1081.
R. Alvarez et al. "Energy-Selective Reconstructions in X-Ray Computerized Tomography" Physics in Medicine and Biology, vol. 21, No. 5 (1976), pp. 733-744.
S. Feuerlein et al. "Multienergy Photon-Counting K-Edge Imaging: Potential for Improved Luminal Depiction in Vascular Imaging" Radiology, vol. 249, No. 3 (Dec. 2008), pp. 1010-1016.
S. Leng et al. "Noise Reduction in Spectral CT: Reducing Dose and Breaking the Trade-Off Between Image Noise and Energy Bin Selection" Medical Physics, vol. 38, No. 9 (Sep. 2011), pp. 4946-4956.
S. Seltzer, "Calculation of Photon Mass Energy-Transfer and Mass Energy-Absorption Coefficients" Radiation Research vol. 136 (Nov. 1993), pp. 147-170.
S. Wilderman et al. "Monte Carlo Calculation of X-Ray Spectra Emitted by Various Anode Materials at Low Voltages" Department of Nuclear Engineering, University of Michigan (1995), pp. 1537-1541.
X. Wang et al. "Material Separation in X-Ray CT with Energy Resolved Photon-Counting Detectors" Medical Physics, vol. 38, No. 3 (Mar. 2011), pp. 1534-1546.
Y. Tomita et al. "X-Ray Color Scanner with Multiple Energy Differentiate Capability" New Energy and Industrial Technology Development Organization, (2004), pp. 3733-3737.

\* cited by examiner

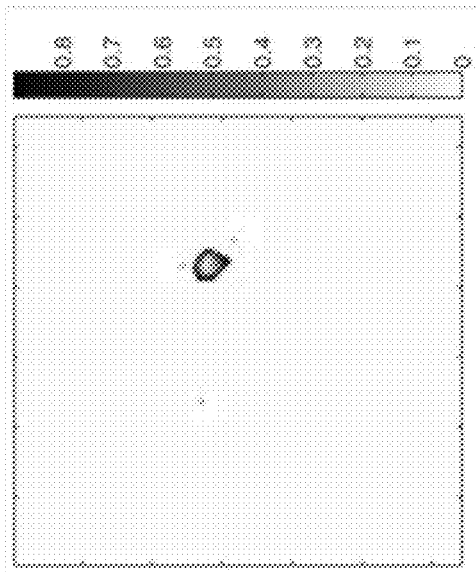
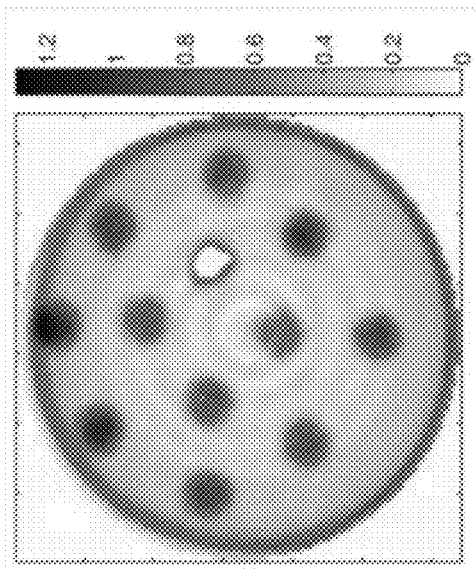
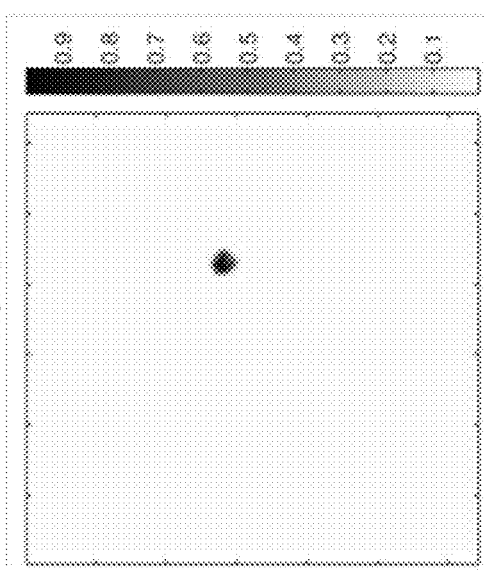
FIG. 10A
FIG. 10B
FIG. 10C
FIG. 10D

SYSTEMS FOR CHARACTERIZING ATHEROSCLEROTIC PLAQUE AND METHODS OF USING SAME

CROSS-REFERENCE TO RELATED APPLICATION

This application claims priority to U.S. Provisional Application No. 61/838,507, filed Jun. 24, 2013, the entire contents of which are incorporated herein by reference and relied upon.

TECHNICAL FIELD

The present technology relates generally to systems for characterizing atherosclerotic plaque, such as a spectral CT system, and methods of using same.

BACKGROUND

Atherosclerotic plaque is commonly assessed by determining the lumen diameter of the relevant portion of the blood vessel. However, lumen diameter is a poor measure of plaque vulnerability. For example, lumen diameter provides no information about the tissue composition of the atherosclerotic plaque itself.

For robust characterization of atherosclerotic plaque, an ideal imaging device would have high spatial resolution to measure plaque morphology, offer multiple tissue classification to determine plaque composition, and be safe for serial studies. Common imaging modalities such as CT, angiography and ultrasound have not been developed to provide detailed characterization of atherosclerotic plaque. Conventional dual-energy CT would provide high resolution, but cannot provide soft tissue classification. In addition, dual-energy CT is not suitable for serial studies because it exposes the test subject to relatively high dose levels of radiation. Improved systems and methods for characterizing atherosclerotic plaques are needed.

BRIEF DESCRIPTION OF THE DRAWINGS

The patent or application file contains at least one drawing executed in color. Copies of this patent or patent application publication with color drawings will be provided by the Office upon request and payment of the necessary fee.

Many aspects of the present technology can be better understood with reference to the following drawings. The relative dimensions in the drawings may be to scale with respect to some embodiments. With respect to other embodiments, the drawings may not be to scale. For ease of reference, throughout this disclosure identical reference numbers may be used to identify identical or at least generally similar or analogous components or features.

FIGS. 10A-10D show quantitative estimates of concentration of adipose (FIG. 10A), water (FIG. 10B), iodine (FIG. 10C) and calcium (FIG. 10D) derived from decomposition of oil phantom images using basis material information only.

DETAILED DESCRIPTION

Figure 1A:
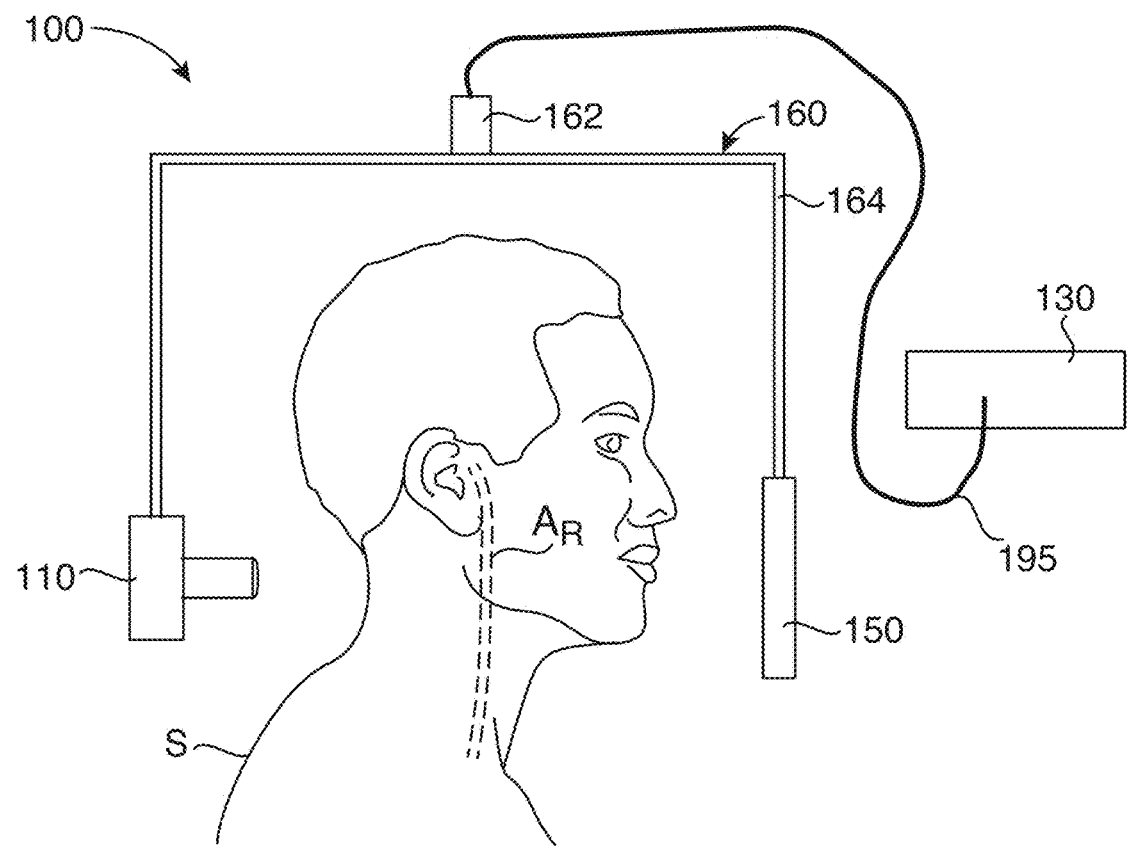
FIG. 1A is a partially schematic, perspective view of a system for characterizing atherosclerotic plaque configured in accordance with one embodiment of the present technology.

The present technology is generally directed to systems for characterizing atherosclerotic plaque, such as a spectral CT system, and methods of using such systems. Atherosclerotic plaque characterization devices consistent with the present technology, for example, may be configured to identify the presence of and/or quantify an amount of one or more soft tissue components in an atherosclerotic plaque. In some embodiments, the soft tissue components comprise water, fat, calcium, iodine, or a combination thereof. In some embodiments, the plaque is located in a blood vessel in the neck of a subject, for example in a carotid artery of the subject.

Predicting arterial plaque rupture has challenged clinicians. Current methods for assessing the risk that atherosclerotic plaque will rupture typically consider only the size, location, and possibly also the shape of an atherosclerotic plaque. However, the composition of the plaque itself has been suggested to provide a more accurate assessment of its stability. Determining the composition of a plaque may also enable clinicians to select and provide a patient with more effective cardiovascular treatments.

Accordingly, the present technology is generally directed to devices, systems, and methods for characterizing atherosclerotic plaque. In one embodiment, for example, a device according to the present technology is configured to determine an identity and/or an amount of one or more components of atherosclerotic plaque. In some embodiments, a method according to the present technology provides characterization of atherosclerotic plaque using a device as disclosed herein.

Specific details of several embodiments of the present technology are described herein with reference to FIGS. 1A-15D. Although many of the embodiments are described herein with respect to atherosclerotic plaque characterization devices and uses thereof, other applications and other embodiments in addition to those described herein are within the scope of the present technology. For example, some embodiments may be useful for quantifying tissue composition in a small field of view in other localized sites. For example, devices and methods disclosed herein may also be useful in assessing tissue composition for assessment of atherosclerosis, rheumatoid arthritis and osteoporosis. Moreover, a person of ordinary skill in the art will understand that embodiments of the present technology can have components and/or procedures in addition to those shown or described herein, and that these and other embodiments can be without several of the components and/or procedures shown or described herein without deviating from the present technology. The headings provided herein are for convenience only.

For ease of reference, throughout this disclosure identical reference numbers are used to identify similar or analogous components or features, but the use of the same reference number does not imply that the parts should be construed to be identical. Indeed, in many examples described herein, the identically-numbered parts are distinct in structure and/or function.

Generally, unless the context indicates otherwise, the terms "distal" and "proximal" within this disclosure reference a position or direction with respect to the treating clinician or clinician's surgical tool (e.g., a surgical navigation registration tool). "Distal" or "distally" are a position distant from or in a direction away from the clinician or clinician's surgical tool. "Proximal" and "proximally" are a position near or in a direction toward the clinician or clinician's surgical tool.

I. Selected Embodiments of Systems for Characterizing Atherosclerotic Plaque

Figure 1B:
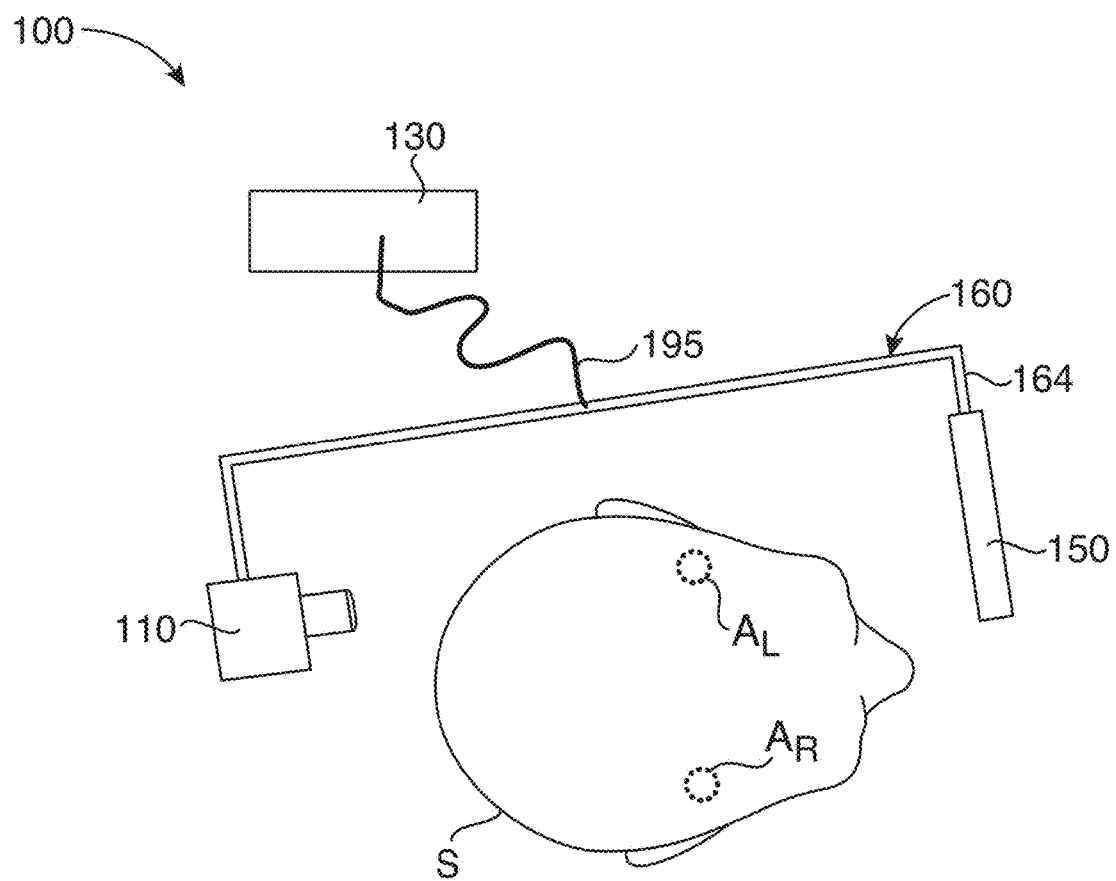
FIG. 1B is a partially schematic, perspective view of the system depicted in FIG. 1A viewed from above.

The present technology is directed to systems and associated methods for characterizing atherosclerotic plaque. FIG. 1A, for example, is a partially schematic, perspective view of a system 100 configured in accordance with an embodiment of the present technology ("system 100"). FIG. 1B is a perspective view of the system 100 depicted in FIG. 1A viewed from above. Referring to FIGS. 1A and 1B together, the system 100 includes a polychromatic energy source 110 ("energy source 110") and a detector 150 configured to detect energy from the energy source 110. The energy source 110 and the detector 150 are arranged about a subject S. The energy source 110 and detector 150 are both in communication with a computer 130 by, for example, one or more wires 195. In some embodiments, the energy source 110 and the detector 150 are connected by a frame 160, which may include one or more arms 164 and a pivot 162. The one or more wires 195 may be housed in the frame 160 (e.g., disposed through the pivot 162 and the one or more arms 164) as required to connect the computer 130 to the energy source 110 and the detector 150. In embodiments where the system 100 is used to characterize atherosclerotic plaque, the energy source 110 and the detector 150 may be arranged to be collinear or substantially collinear with an artery, such as the right carotid artery $A_R$ (FIG. 1A) or the left carotid artery $A_L$ (FIG. 1B) of the subject S. The system 100 is configured to rotate about the subject S (e.g., about the artery $A_R$ or $A_L$) in order to provide three-dimensional data to a clinician.

The energy source 110 may be, for example, a multi-energy x-ray source. Any suitable multi-energy x-ray source may be used, including traditional cathode-anode type x-ray sources. In some embodiments, the multi-energy x-ray source is configured to emit x-ray photons of at least two different energies, for example three different energies, four different energies, five different energies, or more than five different energies. In some embodiments, the multi-energy x-ray source has a small field of view. For example, the x-ray source may be a microfocus x-ray source (e.g., L8121-03, commercially available from Hamamatsu Photonics of Iwata City, Japan).

The detector 150 is configured to detect photons of various energies produced by the energy source 110. For example, the detector 150 may be an energy differentiating type detector configured to simultaneously detect radiation having a plurality of energies. The detector 150 may therefore be configured to detect and count (e.g., sort) photons (e.g., x-rays) having different energies. For example, the detector 150 may be programmed with several energy thresholds to define a plurality of energy ranges (e.g., energy bands), such that each detected photon is determined to have an energy corresponding to one of the defined energy ranges. In some embodiments, the detector 150 is configured to distinguish photons having an energy of 30-45 keV from photons having an energy outside that range. In some embodiments, the detector 150 is configured to distinguish photons having an energy of 45-60 keV from photons having an energy outside that range. In some embodiments, the detector 150 is configured to distinguish photons having an energy of 60-80 keV from photons having an energy outside that range. In some embodiments, the detector 150 is configured to distinguish photons having an energy of 80-100 keV from photons having an energy outside that range. In some embodiments, the detector 150 is configured to distinguish photons having an energy of 100 keV or greater from photons having an energy less than 100 keV. In some embodiments, the detector 150 is configured to distinguish and count (e.g., sort) photons having an energy of 30-45 keV, an energy of 45-60 keV, an energy of 60-80 keV, an energy of 80-100 keV, and/or 100 keV or greater. In some embodiments, the detector 150 is configured to distinguish and count (e.g., sort) photons of at least two energies selected from 30-45 keV, 45-60 keV, 60-80 keV, 80-100 keV, and 100 keV or greater. In some embodiments, the detector 150 is configured to distinguish and count (e.g., sort) photons of at least three energies selected from 30-45 keV, 45-60 keV, 60-80 keV, 80-100 keV, and 100 keV or greater. In some embodiments, the detector 150 is configured to distinguish and count (e.g., sort) photons of at least four energies selected from 30-45 keV, 45-60 keV, 60-80 keV, 80-100 keV, and 100 keV or greater. In some embodiments, the detector 150 is configured to distinguish and count (e.g., sort) photons having energies of 30-45 keV, 45-60 keV, 60-80 keV, 80-100 keV, and 100 keV or greater.

In other embodiments, the detector 150 is configured to distinguish and count (e.g., sort) photons having energies in a predetermined range into an energy band. For example, in some embodiments all detected photons having an energy of 30 keV to 45 keV are counted collectively in a single 30-45 keV energy band. Similarly, in some embodiments all detected photons having an energy of 45 keV to 60 keV are counted collectively in a single 45-60 keV energy band. In some embodiments, all detected photons having an energy of 60 keV to 80 keV are counted collectively in a single 60-80 keV energy band. In some embodiments, all detected photons having an energy of 80 keV to 100 keV are counted collectively in a single 80-100 keV energy band. In some embodiments, all detected photons having an energy of greater than 100 keV are counted collectively in a single >100 keV energy band.

In some embodiments, the detector 150 is configured to distinguish and count (e.g., sort) photons having energies in predetermined energy bands of 30-35 keV, 30-40 keV, 30-45 keV, 30-50 keV, 30-55 keV, 30-60 keV, 30-65 keV, 30-70 keV, 30-75 keV, 30-80 keV, 30-85 keV, 30-90 keV, 30-95 keV, or 30-100 keV. In some embodiments the detector 150 is configured to distinguish and count (e.g., sort) photons having energies in predetermined energy bands of 35-40 keV, 35-45 keV, 35-50 keV, 35-55 keV, 35-60 keV, 35-65 keV, 35-70 keV, 35-75 keV, 35-80 keV, 35-85 keV, 35-90 keV, 35-95 keV, or 35-100 keV. In some embodiments the detector 150 is configured to distinguish and count (e.g., sort) photons having energies in predetermined energy bands of 40-45 keV, 40-50 keV, 40-55 keV, 40-60 keV, 40-65 keV, 40-70 keV, 40-75 keV, 40-80 keV, 40-85 keV, 40-90 keV, 40-95 keV, or 40-100 keV. In some embodiments the detector 150 is configured to distinguish and count (e.g., sort) photons having energies in predetermined energy bands of 45-50 keV, 45-55 keV, 45-60 keV, 45-65 keV, 45-70 keV, 45-75 keV, 45-80 keV, 45-85 keV, 45-90 keV, 45-95 keV, or 45-100 keV. In some embodiments the detector 150 is configured to distinguish and count (e.g., sort) photons having energies in predetermined energy bands of 50-55 keV, 50-60 keV, 50-65 keV, 50-70 keV, 50-75 keV, 50-80 keV, 50-85 keV, 50-90 keV, 50-95 keV, or 50-100 keV. In some embodiments the detector 150 is configured to distinguish and count (e.g., sort) photons having energies in predetermined energy bands of 55-60 keV, 55-65 keV, 55-70 keV, 55-75 keV, 55-80 keV, 55-85 keV, 55-90 keV, 55-95 keV, or 55-100 keV. In some embodiments the detector 150 is configured to distinguish and count (e.g., sort) photons having energies in predetermined energy bands of 60-65 keV, 60-70 keV, 60-75 keV, 60-80 keV, 60-85 keV, 60-90 keV, 60-95 keV, or 60-100 keV. In some embodiments the detector 150 is configured to distinguish and count (e.g., sort) photons having energies in predetermined energy bands of 65-70 keV, 65-75 keV, 65-80 keV, 65-85 keV, 65-90 keV, 65-95 keV, or 65-100 keV. In some embodiments the detector 150 is configured to distinguish and count (e.g., sort) photons having energies in predetermined energy bands of 70-75 keV, 70-80 keV, 70-85 keV, 70-90 keV, 70-95 keV, or 70-100 keV. In some embodiments the detector 150 is configured to distinguish and count (e.g., sort) photons having energies in predetermined energy bands of 75-80 keV, 75-85 keV, 75-90 keV, 75-95 keV, or 75-100 keV. In some embodiments the detector 150 is configured to distinguish and count (e.g., sort) photons having energies in predetermined energy bands of 80-85 keV, 80-90 keV, 80-95 keV, or 80-100 keV. In some embodiments the detector 150 is configured to distinguish and count (e.g., sort) photons having energies in predetermined energy bands of 85-90 keV, 85-95 keV, or 85-100 keV. In some embodiments the detector 150 is configured to distinguish and count (e.g., sort) photons having energies in predetermined energy bands of 90-95 keV or 90-100 keV.

One of skill in the art will recognize that the detector 150 may be configured to distinguish and count (e.g., sort) photons having energies in any combination of predetermined energy bands. In some embodiments, the predetermined energy bands do not overlap, such that the detector 150 is configured to distinguish and count (e.g., sort) each detected photon into exactly one of a plurality of predetermined energy bands. For example, the detector 150 may be configured to distinguish and count (e.g., sort) photons into energy bands of 30-50 keV, 50-65 keV, 65-85 keV, 85-95 keV, or greater than 95 keV. In such an embodiment, a detected photon having an energy of 56 keV would be distinguished and counted (e.g., sorted) into the 50-65 keV energy band.

The energy bands may be defined to correspond to different classes of components typically found in the type of soft tissue being imaged. For example, the energy bands may be selected to correspond to adipose, water, calcium and iodine when the soft tissue is an atherosclerotic plaque. In some embodiments, the detector is a CdTe photon counting detector, such as CdTe radiation line sensor (e.g., C10413, commercially available from Hamamatsu Photonics of Iwata City, Japan).

A photon counting detector offers several advantages over existing dual-energy CT systems. First, strict dual-energy x-ray systems are incapable of providing data for characterizing soft tissue components. In addition, existing dual-energy x-ray systems typically have less efficient energy integrating detectors, requiring high radiation dose levels which limits their use for serially evaluating a soft tissue, such as an atherosclerotic plaque. In contrast, a photon counting detector can provide enough information to characterize components of a soft tissue, and, because of their high detection efficiency, can be operated at relatively low dose levels to allow safe repeated studies of the same subject.

The computer 130 is in communication with the detector 150 and the energy source 110 and is configured to receive data from the detector 150. In some embodiments, the detector 150 is configured to process the detected photons to provide energy differentiated data of the image to the computer 130. The computer 130 is configured to receive the energy differentiated data from the detector 150 and convert it to a linear attenuation value for each energy range at each location of the image.

Linear attenuation at each location in the image ($\vec{x}$) and at each energy (e), $\mu(e, \vec{x})$, can be represented as a linear combination of the mass attenuation coefficients of each component material, $f_m(e)$, as:

$$\mu(e, \vec{x}) = \sum_{m=1}^{M} \rho_m(\vec{x}) f_m(e)$$

In some embodiments, the computer 130 is configured to calculate the linear attenuation at each location in the image and at each energy range. The computer 130 is also configured to display the linear attenuation at each location in the image separately for each of the energy ranges. The resulting images correspond to the components of the sample (e.g., the atherosclerotic plaque) based on their unique linear attenuation values.

In some embodiments, the computer 130 is further configured to provide a report (e.g., a printed report or a report in an electronic format) to a clinician. The report includes information about the components of the sample (e.g., atherosclerotic plaque), such as the total concentration of each components of the sample (e.g., adipose, water, iodine and calcium) and/or the image corresponding to each energy range.

In some embodiments, the computer 130 is configured to enable (e.g., prompt) a clinician to input the type of soft tissue to be characterized before the sample is irradiated with polychromatic energy. The computer 130 may include a memory device programmed to correlate the soft tissue type input with a list (e.g., table) of energy threshold values useful for characterizing common components of the input soft tissue type. The computer 130 may therefore also provide one or more threshold energy values to the detector 150 to define two or more energy ranges. Alternatively, the energy threshold values may be input into the computer 130 or detector 150 manually (e.g., with or without inputting a type of soft tissue).

The computer 130 may also be configured to control the energy source 110, for example, by controlling the voltage, current, focal spot size, and/or beam angle. In some embodiments, the computer 130 may select a voltage, current, focal spot size and/or beam angle based on input of the soft tissue type to be characterized, for example, by referring to a lookup table stored in a memory component of the computer 130. Alternatively, the voltage, current, focal spot size and/or beam angle may be manually set on the energy source 110.

Figure 2:
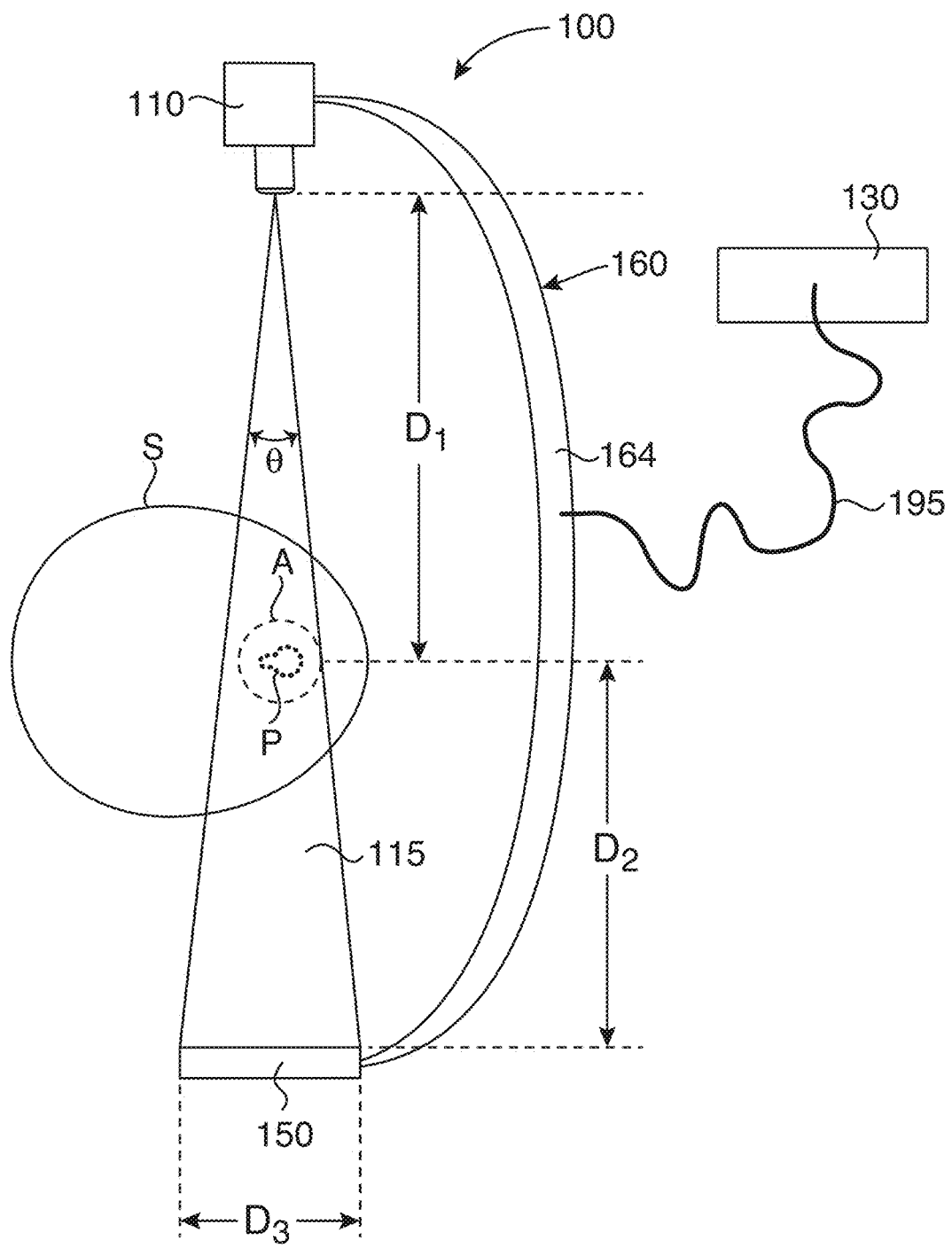
FIG. 2 is a partially schematic top view of the system of FIGS. 1A and 1B for characterizing atherosclerotic plaque.

Referring now to FIG. 2, the system 100 may be configured to rotate about the sample S and an artery A of the sample S that includes plaque P. In the illustrated embodiment, the system 100 is configured such that the energy source 110 is a distance $D_1$ from the artery A. The distance $D_1$ is at least as long as the focus-to-object distance ("FOD") of the energy source 110. The detector 150 is a second distance $D_2$ from the artery A such that substantially all of the energy beam 115 is detectable by the detector 150. The system 100 is configured to rotate about the source S such that the energy source 110 and the detector 150 are substantially the same distances $D_1$ and $D_2$, respectively, from the artery A (i.e., the artery A defines an axis of rotation for the system 100). Further, in some embodiment the system 100 can be configured to dynamically adjust distance $D_1$ and/or distance $D_2$ in order to change the size and location of the imaging field-of-view.

In some embodiments, the system 100 is configured to acquire tomographic data, for example CT x-ray data, of the sample (e.g., atherosclerotic plaque P). Accordingly, the system 100 may be configured to rotate and translate the energy source 110 and the detector 150 with respect to the sample (e.g., atherosclerotic plaque P). The computer 130 may be configured to control the rotation and translation of the system 100. In other embodiments, however, the translation/rotation of the system 100 may be controlled using other suitable mechanisms.

II. Selected Methods for Characterizing an Atherosclerotic Plaque

Figure 3:
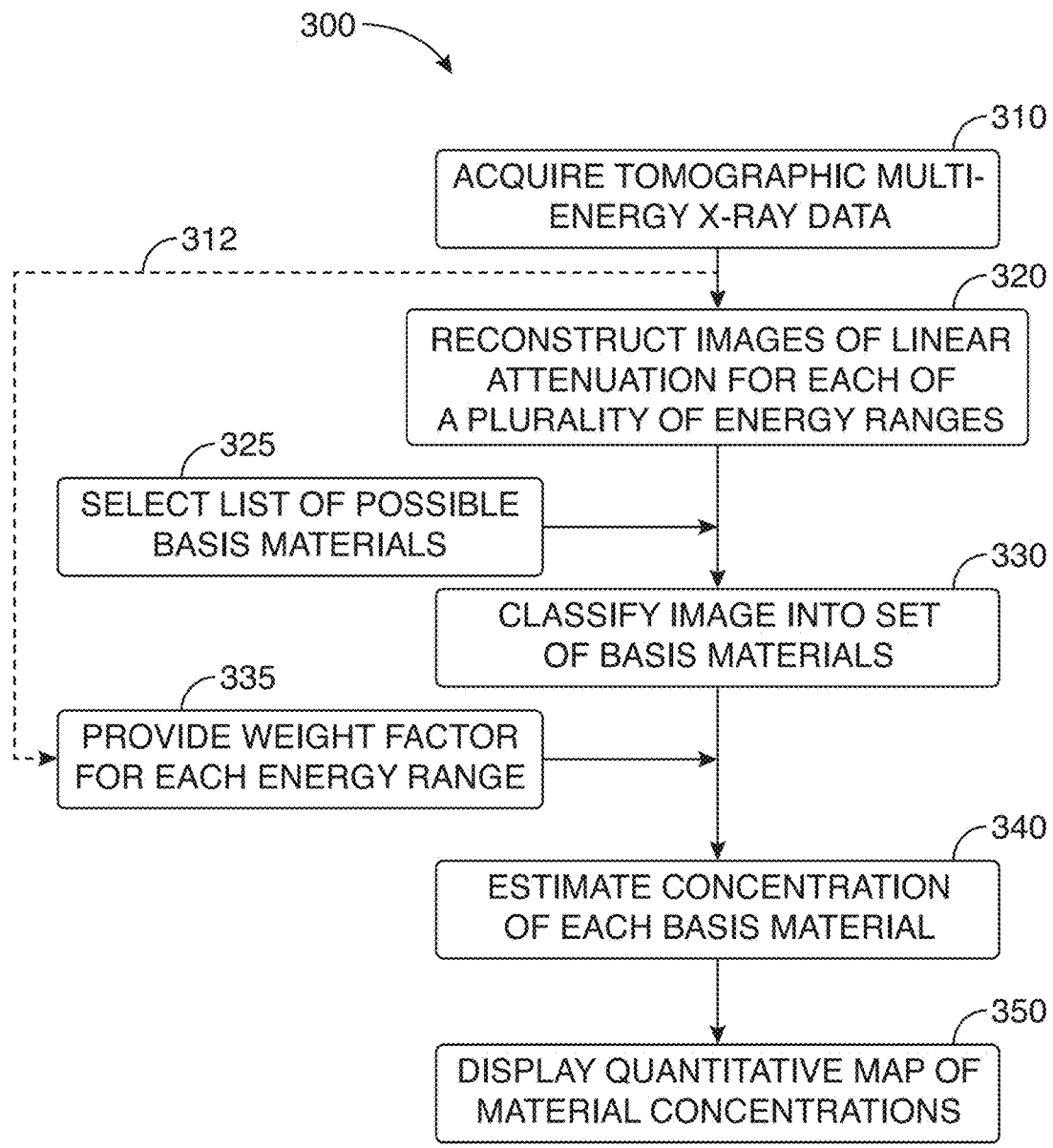
FIG. 3 depicts steps of a method for characterizing atherosclerotic plaque in accordance with one embodiment of the present technology.

FIG. 3 is a flow diagram illustrating a method 300 of characterizing atherosclerotic plaque based on tomographic multi-energy x-ray data according to the present technology. The method 300 may be carried out using the system 100 described above with reference to FIGS. 1A-2 or other suitable systems. The method 300 begins at step 310 by acquiring tomographic multi-energy x-ray data. In step 320, images of linear attenuation for each of the energy ranges are reconstructed. Based on the list of possible basis materials (e.g., components of the atherosclerotic plaque) selected in step 325, each image is classified into a set of basis materials in step 330. To enable comparison of data between the images, a weight factor for each energy range is provided (e.g., from the tomographic multi-energy x-ray data provided in step 310 or from other known characteristics of x-ray transmission and/or detection), and used to estimate the concentration of each basis material in step 340. The resulting quantitative maps of the basis material concentrations are then displayed to a user (e.g., a clinician) in step 350.

Reconstruction of the images of linear attenuation in step 320 may be accomplished by a number of techniques. In one method (the "basis only" method), linear attenuation at each location in the image $\vec{x}$ is represented as a linear combination of photoelectric and Compton cross-sections and, when the sample includes a K-edge discontinuity, a K-edge component:

$$\mu(e, \vec{x}) = \alpha_{ph}(\vec{x}) f_{ph}(e) + \alpha_C \vec{x} f_C(e) + \alpha_K(\vec{x}) f_K(e),$$

wherein each contribution α is from basis functions defines as the energy dependent photoelectric ($f_{ph}$), Compton ($f_C$) and K-edge ($f_K$) component (from materials such as iodine or gadolinium) attenuation. The multi-energy data provided in step 310 can thus be directly decomposed into basis images once the optimal values of α are known. In one method, the α values are determined by weighted least squares estimation of each basis material's contribution, for example using the following equation:

$$\hat{a}(\vec{x}) = \arg_{\vec{\alpha}} \min \sum_{e=1}^{E} \left[ \left( \hat{\mu}(e, \vec{x}) - \sum_{b=1}^{B} \alpha_b(\vec{x}) f_b(e) \right)^2 W_e \right]$$

wherein $\hat{\mu}(e, \vec{x})$ is an estimate of the linear attenuation coefficient at energy range e from the reconstructed multi-energy images, B is the number of basis materials (e.g., components), and E is the number of energy ranges, and $W_e$ are weights that account for variable confidence in information from each energy range e based on the number of photons counted in each energy range e. Thus, $\hat{\mu}(e, \vec{x})$ can be estimated at any energy, and can then be decomposed into concentrations of each material of interest as further described below.

In one variation, the basis method described immediately above is performed using a preselected list of basis materials that are possibly present at each location $\vec{x}$ of the image (the "class+basis" method).

In another embodiment, the step 320 of reconstructing images of linear attenuation includes decomposing the multi-energy data from step 310 directly into materials of interest without forming basis images first (the "material" method). Such embodiments reduce the risk that information might be lost due to non-orthogonality of the basis functions. Accordingly, in the material method, the multi-energy images can be directly decomposed into material images according to the following equation:

$$\hat{\rho}(\vec{x}) = \arg_{\rho \geq 0} \min \sum_{e=1}^{E} \left[ \left( \hat{\mu}(e, \vec{x}) - \sum_{m=1}^{M} \rho_m(\vec{x}) f_m(e) \right)^2 W_e \right]$$

wherein mass attenuation coefficients ($f_m$) of materials of interest are used instead of physical basis functions. In some embodiments, the material method is employed in step 320 with a predetermined list of materials of interest (e.g., components of the soft tissue to be characterized). Such a method offers the favorable property of being able to enforce non-negativity of the concentration estimates since negative contributions from component materials is not physically meaningful.

In some embodiments, the step 320 includes using the material method described above, with an additional step of predetermining (e.g., pre-selecting) a list of materials for each image location $\vec{x}$ that includes only those present in its class. The list of materials may be predetermined based on a priori knowledge of materials likely to be present. Alternatively, the list of materials may be predetermined based on the amount of x-ray photons detected in that energy range.

Initial classification of each region of the images can be accomplished by any suitable method. In some embodiments, initial classification is automatically performed based on differences in measured linear attenuation coefficients at each energy range. In such embodiments, the mean difference in attenuation between all energy ranges at each voxel is defined as follows:

$$\text{mean difference} = \sum_{e_1=1}^{E} \sum_{e_2=e+1}^{E} [(\hat{\mu}(e_1, \vec{x}) - \hat{\mu}(e_2, \vec{x}))] / [0.5E(E-1)]$$

and is plotted versus the weighted mean of the linear attenuation defined as:

$$\sum_{e=1}^{E} W_e \hat{\mu}(e, \vec{x}) / E$$

Using the above-described initial classification method, multi-dimensional data (e.g., 5-dimensional data resulting from tomographic data from five energy ranges) can be reduced to two dimensions. The resulting two-dimensional data differentiates materials based on unique changes in $\mu$ and the absolute value of $\mu$ at each energy range.

Figure 5:
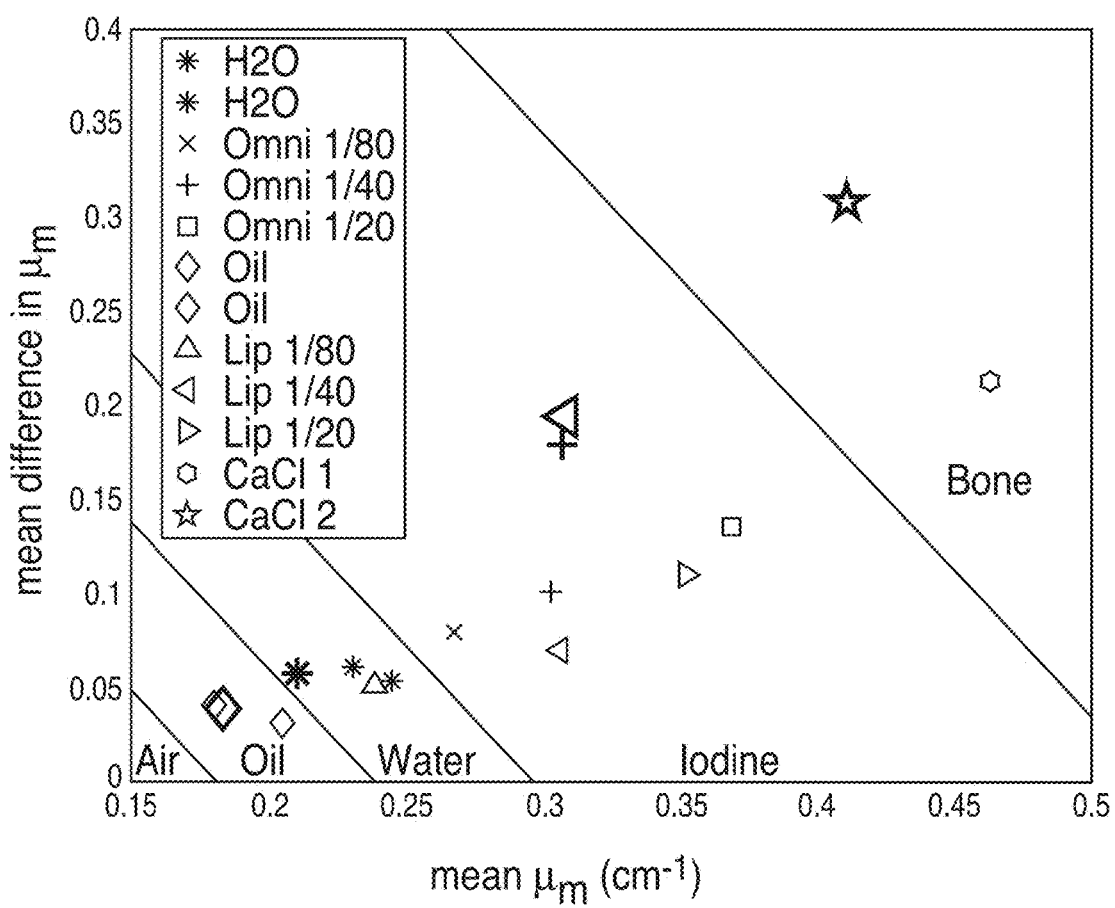
FIG. 5 illustrates one simple difference classifier based on a plot of mean difference ($\mu_m$) as a function of mean $\mu_m$.
Figure 6A:
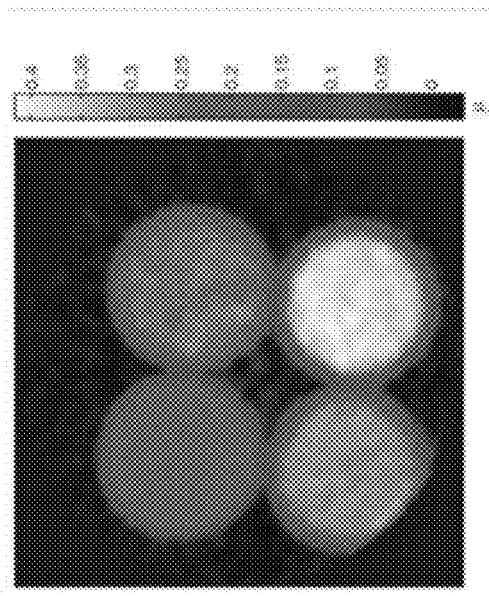
FIGS. 6A-6D show transaxial reconstructed images of linear attenuation (1/cm) for an iodine phantom for four energy ranges: 30-45 keV (FIG. 6A), 45-60 keV (FIG. 6B), 60-80 keV (FIG. 6C), and 80-100 keV (FIG. 6D).
Figure 6B:
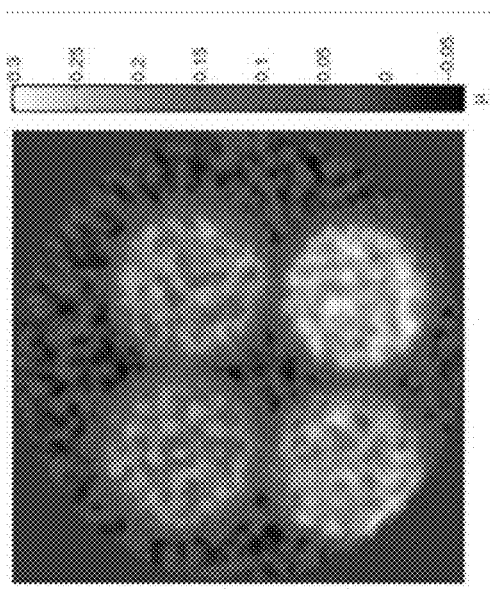
Figure 6C:
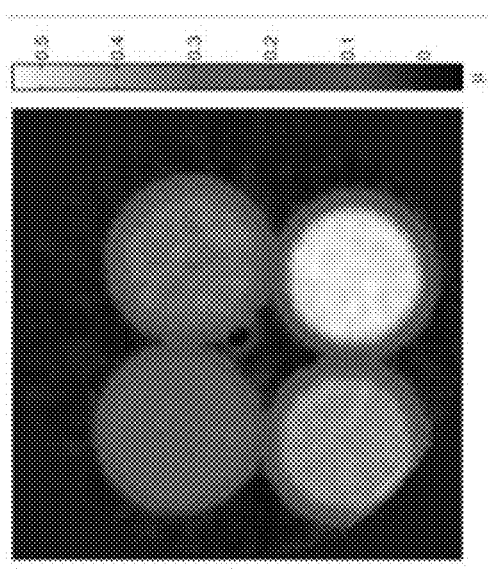
Figure 6D:
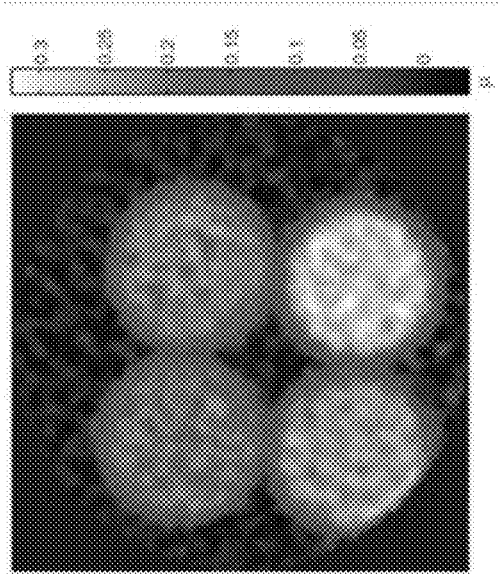

For example, as shown in FIG. 5, automatic initial classification of air, oil, water, iodine and bone is possible based on the uniqueness of each material in both mean difference in $\mu_m$ and in absolute value of mean $\mu_m$. In FIG. 5, large icons correspond to theoretical $\mu$ for each material. Accordingly, each voxel in an image can be segmented into classes of materials (e.g., "adipose+water"; "adipose+water+iodine"; "calcium+water" etc.). When the soft tissue to be characterized is atherosclerotic plaque, voxels mapped to the oil or water region can be classified as "adipose+water"; while voxels mapped to the iodine region can be classified as "adipose+water+iodine." Voxels mapped to the bone region can be classified as "calcium+water."

Energy ranges can be selected based on the soft tissue to be characterized, including the common components of that soft tissue type. For example, atherosclerotic plaques commonly include adipose, water, calcium and iodine (from contrast agent). Nonetheless, the methods and systems disclosed herein are capable of characterizing atherosclerotic plaques without the use of a contrast agent.

III. Examples

Example 1

System for Ex Vivo Characterization of Atherosclerotic Plaques

Figure 4:
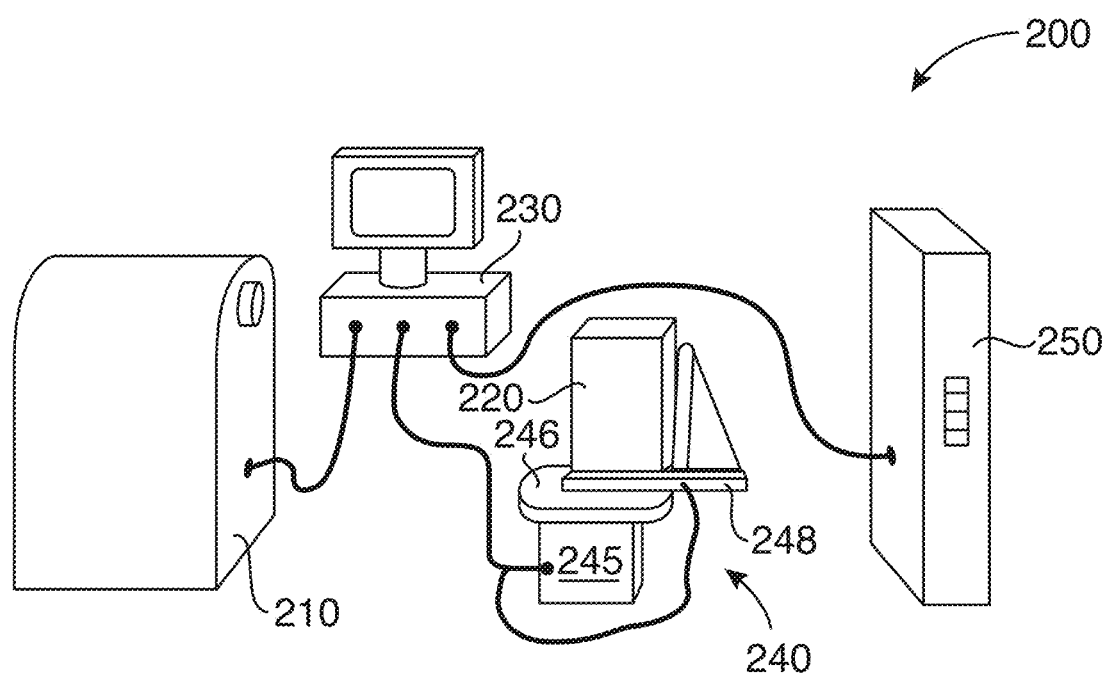
FIG. 4 is a perspective view of another system for characterizing an ex vivo atherosclerotic plaque model configured in accordance with another embodiment of the present technology.

FIG. 4 illustrates a photon-counting CT x-ray system 200 for interrogation of single carotid arteries. The system 200 includes a computer 230 in communication with a microfocus multi-energy x-ray source 210 and an energy differentiating detector 250. The x-ray source 210 was catalog number L8121-03 (commercially available from Hamamatsu Photonics of Iwata City, Japan), having a tube voltage of 40-150 kV, a tube current of 10-500 μA, a maximum output of 75 W, a minimum x-ray focal spot size of 5 μm, a maximum x-ray beam angle of 43°, and a focus-to-object distance of 17 mm. The x-ray source was operated at 120 kVp at 7 μA with a 20 μm focal spot. The low tube current was selected to minimize effects of pulse-pileup, deadtime, and energy response distortion, as well as to assess the ability of a system according to the present technology to accurately characterize atherosclerotic plaques while exposing a subject to a low radiation dose.

The detector 250 was catalog number C10413 (commercially available from Hamamatsu Photonics of Iwata City, Japan) featuring a 64-channel CdTe radiation line sensor including 64 pixels each 0.8 mm wide by 0.5 mm deep by 1 mm high at 1 mm pitch. The detector 250 was configured to categorize incoming photons into one of five energy ranges: 30-45 keV, 45-60 keV, 60-80 keV, 80-100 keV, or >100 keV.

A sample platform 240 was located between the x-ray source 210 and the detector 250, and included a riser 245 and a rotating platform 246 upon which a 1-mm incremental translation mechanism 248 was mounted. The sample holder 220 was thus capable of being rotated and translated to support step-and shoot acquisition of multiple slices of tomographic data.

Example 2

Characterization of Iodine Phantom Test Object 12 mm vials containing water (no iodine), and intravenous iodine contrast agent (Omnipaque®, GE Healthcare) diluted 1/80, 1/40 and 1/20 in water were scanned using the system of Example 1 with 64 radial bins and 160 azimuthal angles per 360°. Images were reconstructed with a fan-beam FBP method with the ramp filter.

The theoretical linear attenuation coefficient for the energy ranges for each dilution was calculated and compared with the measured linear attenuation coefficient from the system of Example 1. Sample images are shown in FIGS. 6A-6D for 30-45 keV, 45-60 keV, 60-80 keV, and the 80-100 keV energy ranges, respectively. The average percent bias in measurements of linear attenuation compared to theoretical values is shown in Table 1, below:

TABLE 1

| Energy Range (keV) | 1/80 Dilution | 1/40 Dilution | 1/20 Dilution | Average absolute bias |
|---|---|---|---|---|
| 30-45 | −16 +/− 0.88 | −22 +/− 0.77 | −30 +/− 0.73 | 23 +/− 5.8 |
| 45-60 | −4.7 +/− 0.8 | −5.2 +/− 0.7 | −4.5 +/− 0.81 | 4.8 +/− 2.4 |
| 60-80 | −3 +/− 1.3 | −0.26 +/− 1.1 | −1.8 +/− 1 | 3.9 +/− 5 |
| 80-100 | −0.51 +/− 1.8 | 3.1 +/− 1.3 | 5.1 +/− 1.6 | 6.6 +/− 8.3 |
| >100 | 2.8 +/− 2.5 | 14 +/− 2.4 | 14 +/− 2/.4 | 14 +/− 14 |

Example 3

Characterization of Oil Phantom Test Object

Twelve cylindrical plastic vials (3.3 mm outer diam.; 2.1 mm inner diam.) were prepared with solutions shown in Table 2 below.

TABLE 2

| Sample | Solution | Density (g/cc) |
|---|---|---|
| 1 | Water only | 1.000 |
| 2 | Water only | 1.000 |
| 3 | Omnipaque ® 1/80 in saline | 1.005 |
| 4 | Omnipaque ® 1/40 in saline | 1.010 |
| 5 | Omnipaque ® 1/20 in saline | 1.020 |
| 6 | Poppyseed only | 0.925 |
| 7 | Poppyseed only | 0.925 |
| 8 | Lipiodol ® 1/80 in poppyseed oil | 0.929 |
| 9 | Lipiodol ® 1/40 in poppyseed oil | 0.934 |

TABLE 2-continued

| Sample | Solution | Density (g/cc) |
|---|---|---|
| 10 | Lipiodol ® 1/20 in poppyseed oil | 0.943 |
| 11 | Calcium chloride in water 0.26 g/cc | 1.117 |
| 12 | Calcium chloride in water 0.51 g/cc | 1/234 |

All objects were scanned using the system of Example 1 with 64 radial bins and 160 azimuthal angles per 360°. Images were reconstructed with a fan-beam FBP method with the ramp filter.

Figure 7:
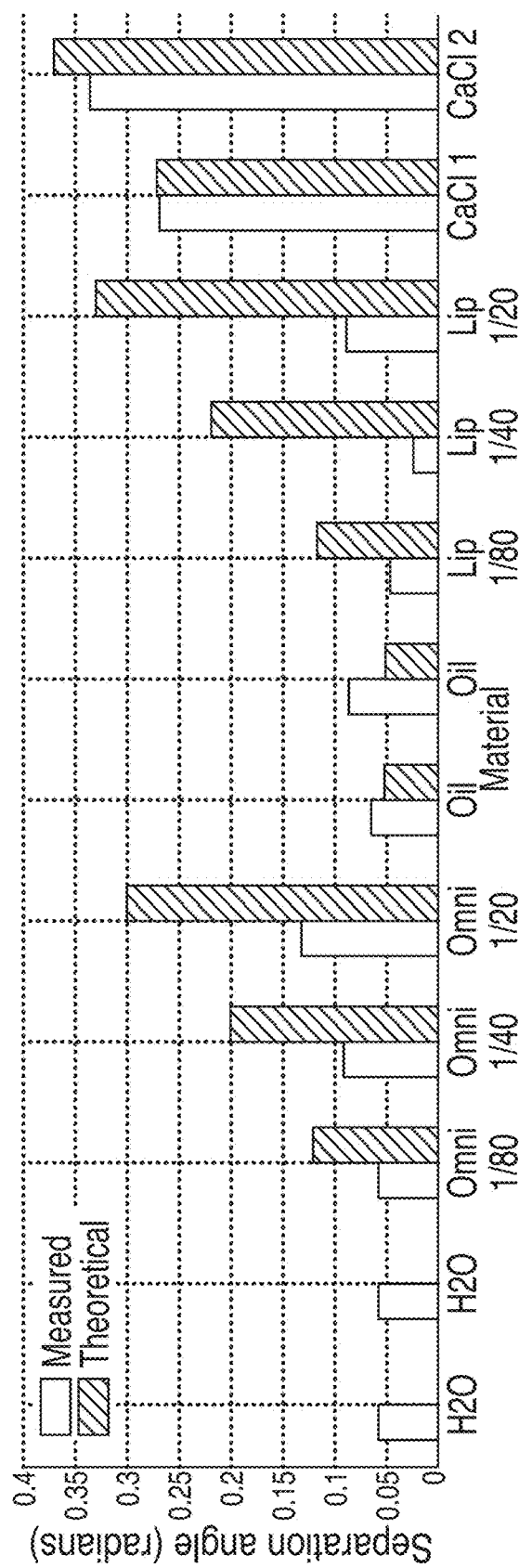
FIG. 7 compares measured separation angles (dark bars) to theoretical separation angles (lighter bars) for water basis material and a variety of test solutions in the oil phantom.

The angle of separation between water and each sample is shown in FIG. 7. The darker band on the left of each pairing shows the measured angle of separation, while the lighter bar on the right of each pairing shows the theoretical angle of separation based on the five energy bands used during acquisition and the assumption of a non-overlapping energy response. Significantly, these data show that water and oil can be separated both theoretically and using the methods disclosed herein. The iodine-based contrast agents (Omnipaque®, Lipiodol®) each featured large theoretical angles of separation (>0.1 radians), but much smaller measured angles of separation (<0.1 radians).

Figure 8:
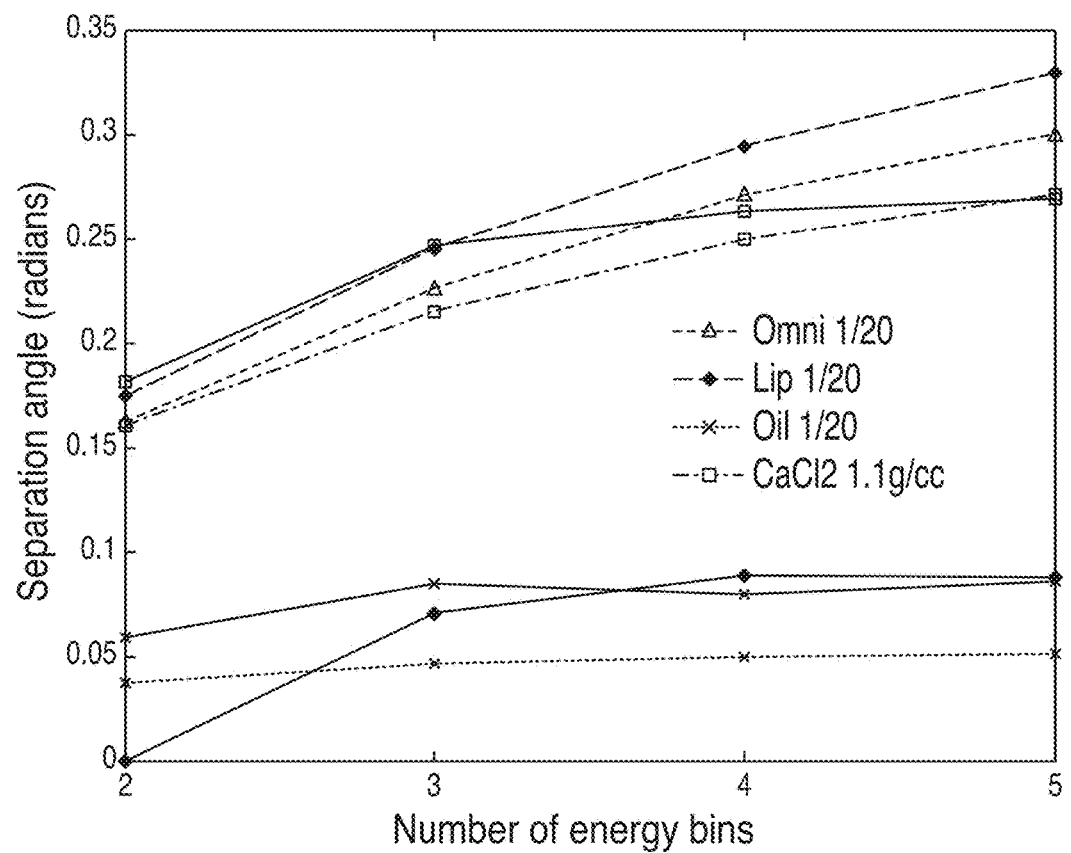
FIG. 8 is a plot of separation angle (radians) as a function of the number of energy bins between water basis material and (i) a 1:20 dilution of iodine-based contrast agent in water (triangles), (ii) a 1:20 dilution of Lipiodol in oil (diamonds), (iii) oil (—x—), and (iv) calcium chloride in water (1.1 g/cc, squares). Theoretical separation angles are shown in dashed lines; actual measured separation angles are shown in solid lines.

The theoretical (dashed lines) and actual (solid lines) dependence of separation angle on the number of energy bins for four materials is shown in FIG. 8. In general, fewer energy bins results in smaller angles of separation. This indicates that separability decreases slightly when information from the higher energy bands is removed from the vectors.

Figure 9A:
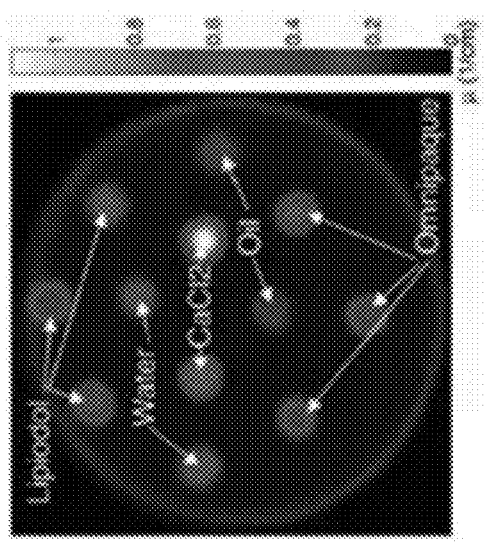
FIGS. 9A-9E show transaxial slices of oil phantom showing linear attenuation coefficients (1/cm) for each of five energy ranges: 30-45 keV (FIG. 9A), 45-60 keV (FIG. 9B), 60-80 keV (FIG. 9C), 80-100 keV (FIG. 9D), and >100 keV (FIG. 9E).
Figure 9B:
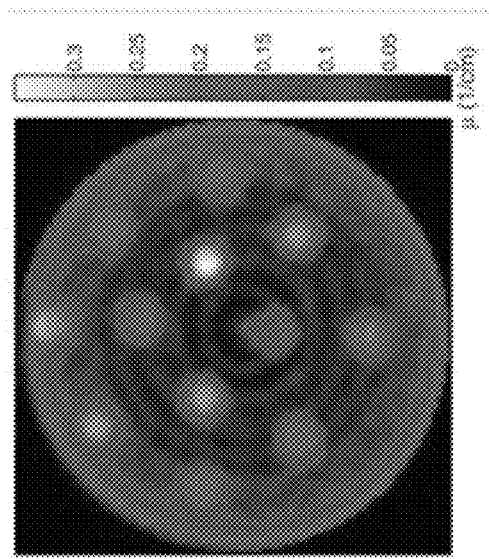
Figure 9C:
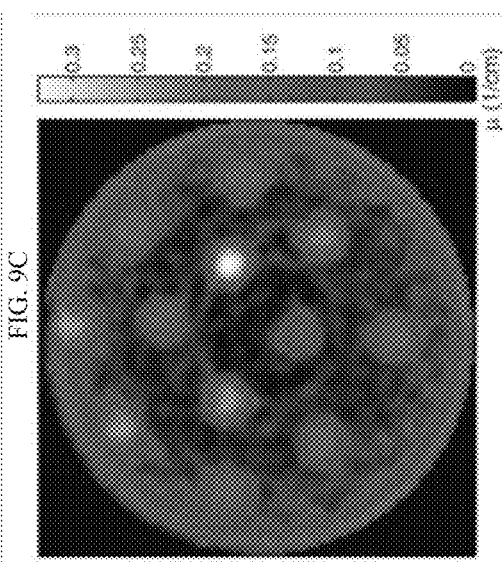
Figure 9D:
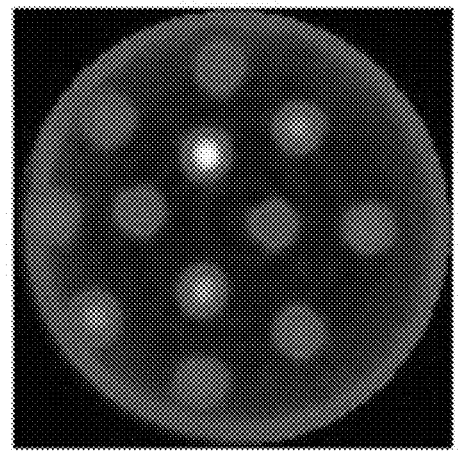
Figure 9E:
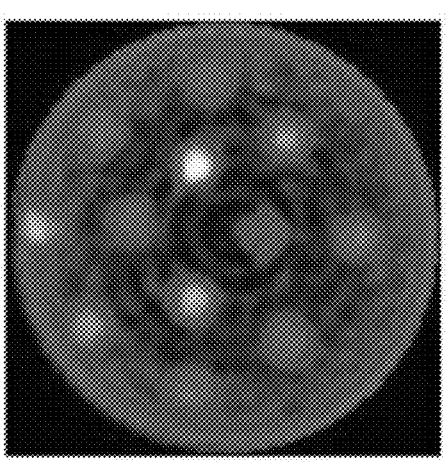

FIGS. 9A-9E show transaxial slices of the twelve oil phantom samples, arranged spatially as shown in FIG. 9A. Each image provides quantitative linear attenuation coefficients for each sample in units of 1/cm. The mean bias compared to theory across all materials and energies was 3%+/−4%. To compare absolute error in concentration measurements, the data was analyzed using the four decomposition methods described above; results are shown in Table 3, below:

TABLE 3

| | Region | | | | |
|---|---|---|---|---|---|
| Method | Water (g/cc) | Oil (g/cc) | Iodine (g/cc) | CaCl$_2$ (g/cc) | Total (g/cc) |
| Basis only | 0.46 +/− 0.50 | 0.04 +/− 0.09 | 0.25 +/− 0.41 | 0.33 +/− 0.35 | 0.27 +/− 0.48 |
| Material only | 0.28 +/− 0.31 | 0.02 +/− 0.05 | 0.31 +/− 0.44 | 0.26 +/− 0.29 | 0.25 +/− 0.44 |
| Basis + Class | 0.03 +/− 0.05 | 0.09 +/− 0.17 | 0.20 +/− 0.26 | 0.32 +/− 0.36 | 0.17 +/− 0.31 |
| Material + Class | 0.06 +/− 0.09 | 0.08 +/− 0.14 | 0.18 +/− 0.25 | 0.32 +/− 0.35 | 0.17 +/− 0.30 |

The data in Table 3 were obtained from 1 mm$^2$ circular regions of interest centered on each feature.

FIGS. 10A-10D show representative material images for the basis only method. Notably, this method failed to provide estimates of material concentration for adipose and water materials. The material only method also similarly failed to provide suitable material concentration estimates (data not shown).

Figure 11C:
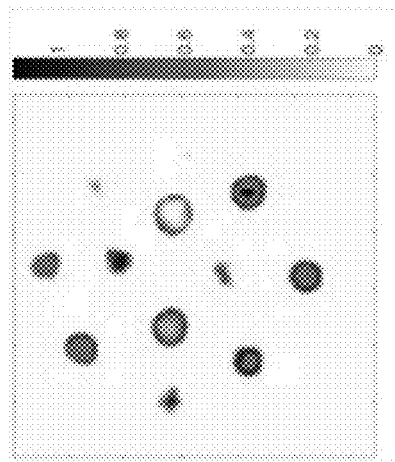
FIGS. 11A-11E show quantitative estimates of concentration of adipose (FIG. 11B), water (FIG. 11C), iodine (FIG. 11D) and calcium (FIG. 11E) derived from decomposition of oil phantom images using both material and classification information. A class image is shown in FIG. 11A.
Figure 11B:
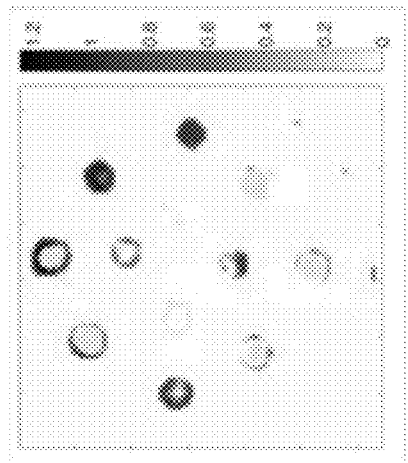
Figure 11E:
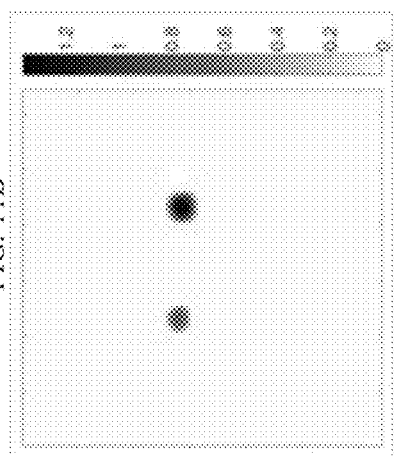
Figure 11A:
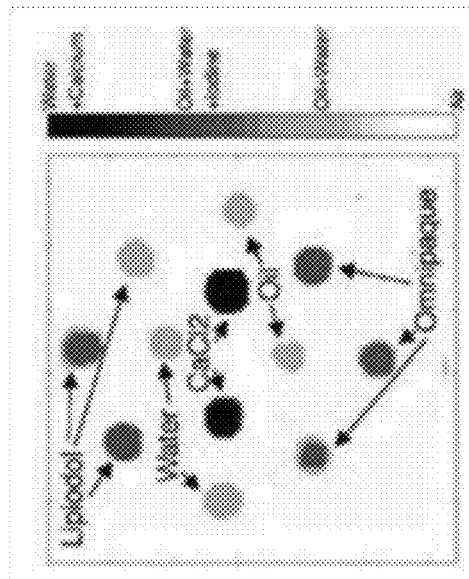
Figure 11D:
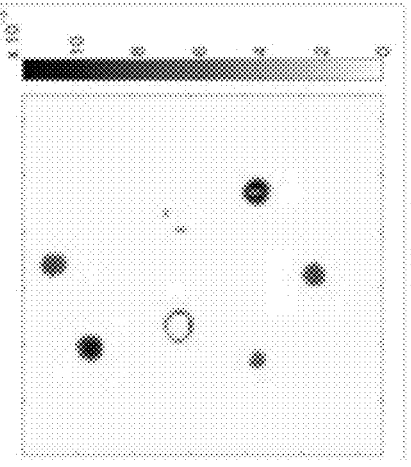
Figures 12A, 12B, 12C, 12D, 12E:
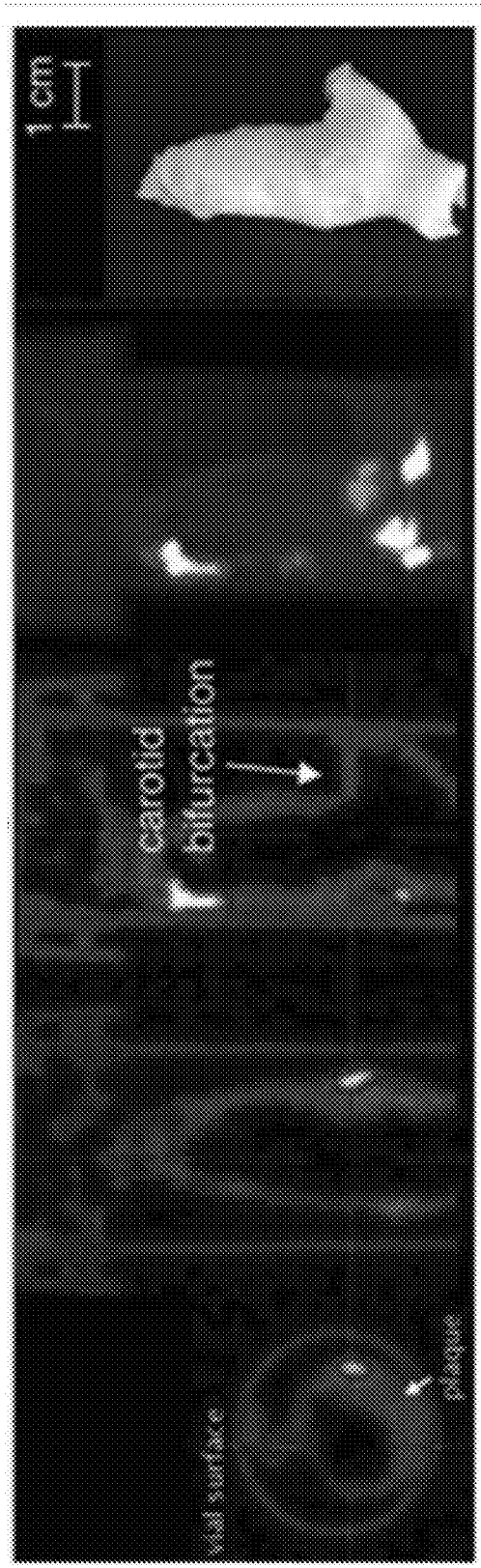
FIGS. 12A-12E show transaxial (FIG. 12A), a coronal (FIG. 12B), a sagittal (FIG. 12C) and a MIP (FIG. 12D) views of volumetric reconstructions of a carotid plaque specimen using photons detected at 30-45 keV. A photograph of the plaque specimen is shown in FIG. 12E in the same orientation as the sagittal view of FIG. 12C.

FIGS. 11A-11E show representative images for the material+class method. FIG. 11A shows the class image, while FIGS. 11B-11E show images for adipose, water, iodine, and calcium classes, respectively. These data indicate that the simple difference classifier described with respect to FIG. 5 is capable of classifying the materials accurately for all regions inside the vials except for one vial containing Lipiodol at the 2-o'clock position of FIG. 11A. It is possible that the failure to classify that one vial was due to its proximity to the edge of the field of view, rather than the method itself. The centers of the vial images were chosen to avoid classification and quantification errors that appear at the boundaries of the vials. It is believed that these errors may be attributable to the thickness (0.6 mm) of the vial walls and/or the limited resolution of the detector 250. Water material was correctly represented in all vials except the Lipiodol solution vials. The oil-only vials were accurately discriminated and quantified.

Example 4

Characterization of Carotid Plaque Specimen

Carotid plaque specimens A and B obtained from carotid endarterectomy surgical procedures were scanned using the system of Example 1 with 64 radial bins and 160 azimuthal angles per 360°. Acquisition time per slice was 35 seconds; multiple slices were acquired with 1 mm spacing. Total acquisition time was 27 minutes per specimen. Images were reconstructed with a fan-beam FBP method with the ramp filter.

Figure 13:
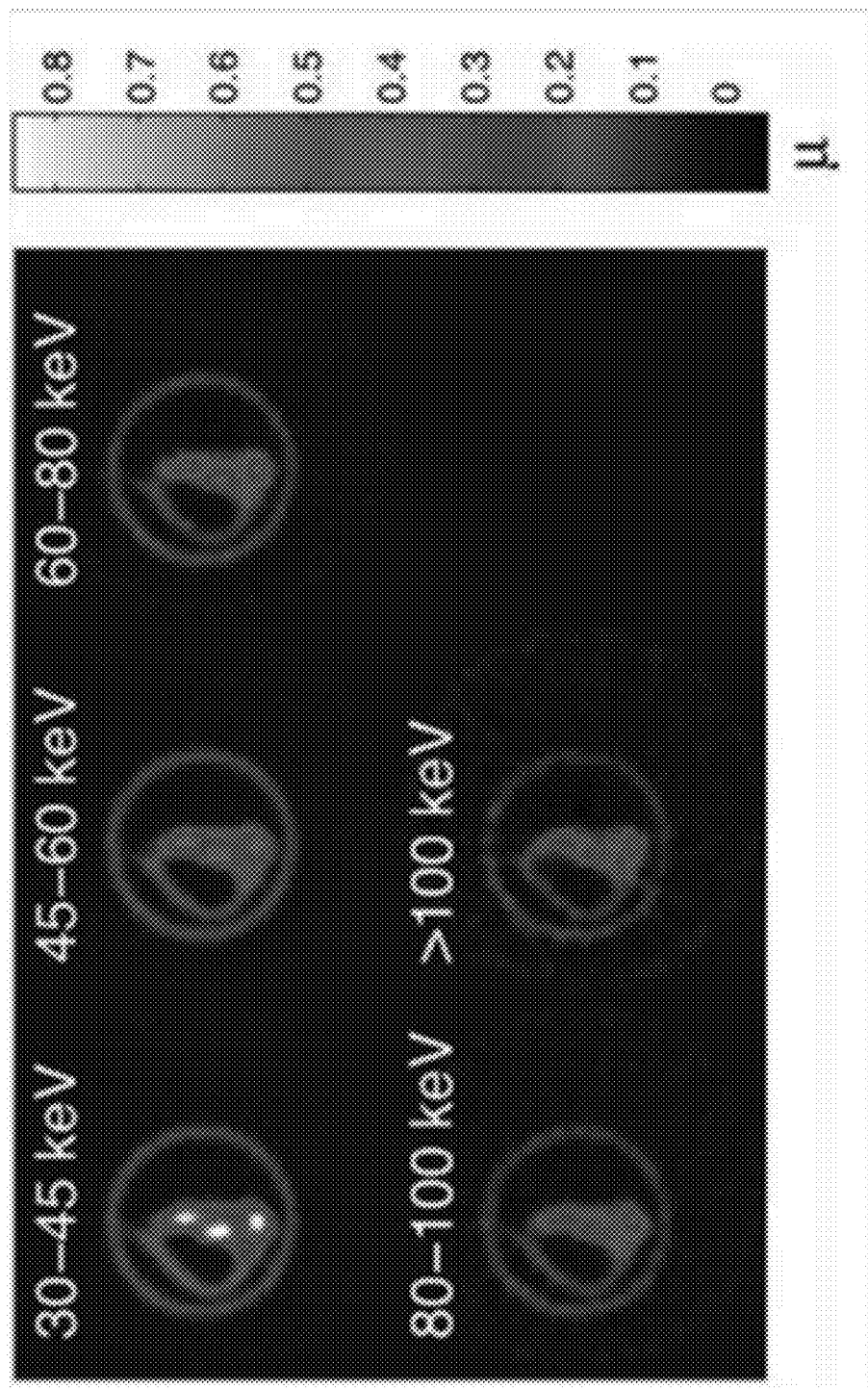
FIG. 13 shows a transaxial view of another plaque specimen at 30-45 keV, 45-60 keV, 60-80 keV, 80-100 keV, and >100 kEV, all acquired simultaneously in accordance with a system and a method of the present technology.
Figure 14A:
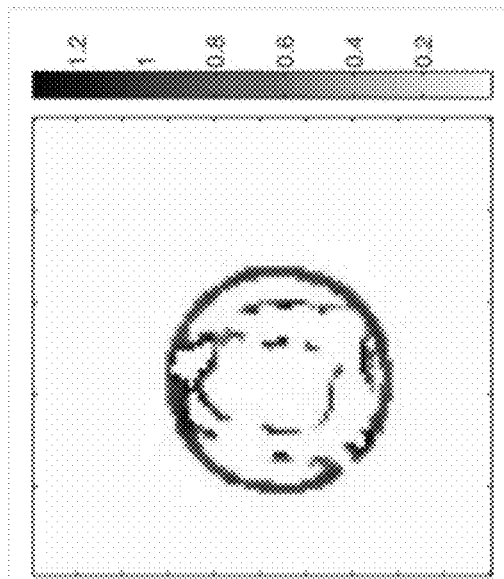
FIGS. 14A-14D show quantitative estimates in g/mL of concentration of adipose (FIG. 14B), water (FIG. 14C), and calcium (FIG. 14D) derived from decomposition of images of the plaque specimen of FIG. 12 using both material and classification information. A classification image (FIG. 14A) was derived from the difference classifier of FIG. 5.
Figure 14B:
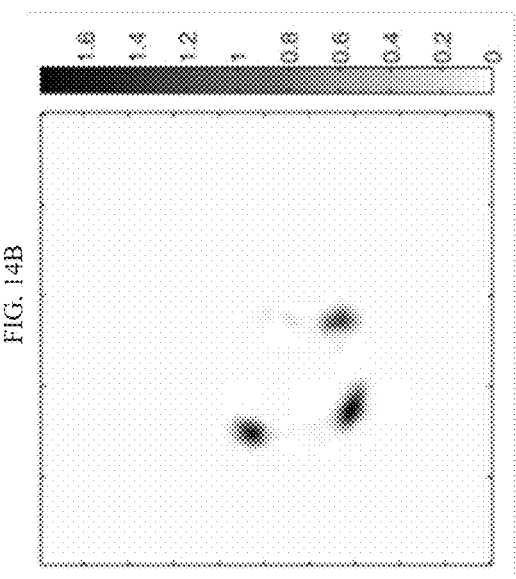
Figure 14C:
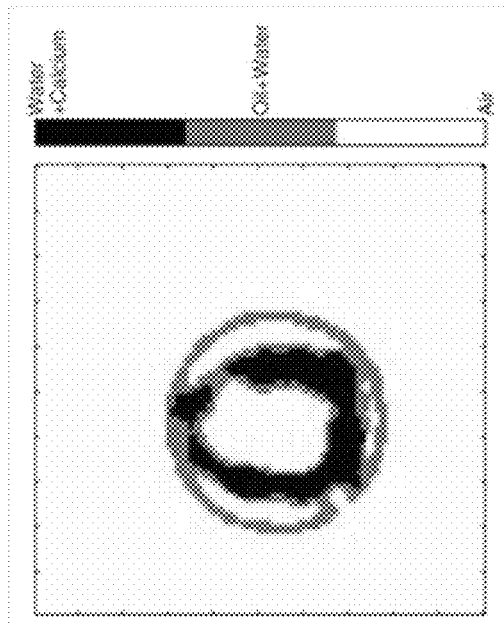
Figure 14D:
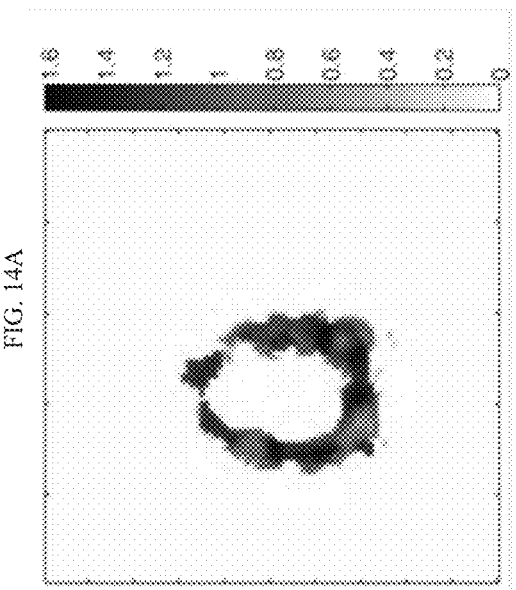
Figure 15A:
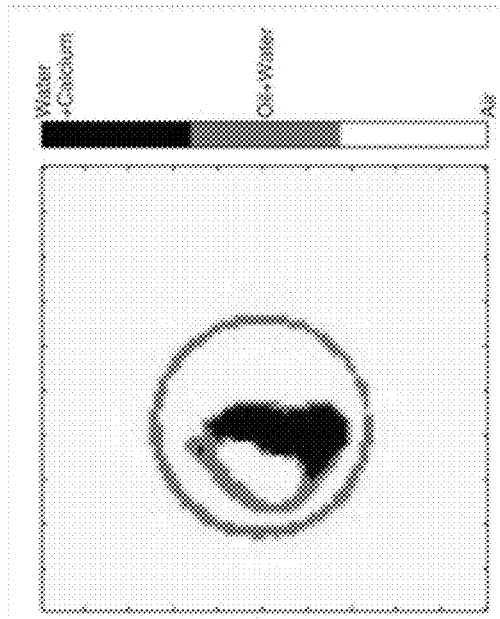
FIGS. 15A-15D show quantitative estimates of concentration of adipose (FIG. 15B), water (FIG. 15C), and calcium (FIG. 15D) derived from decomposition of images of the plaque specimen of FIG. 13 using both material and classification information. A classification image (FIG. 15A) was derived from the difference classifier of FIG. 5.
Figure 15B:
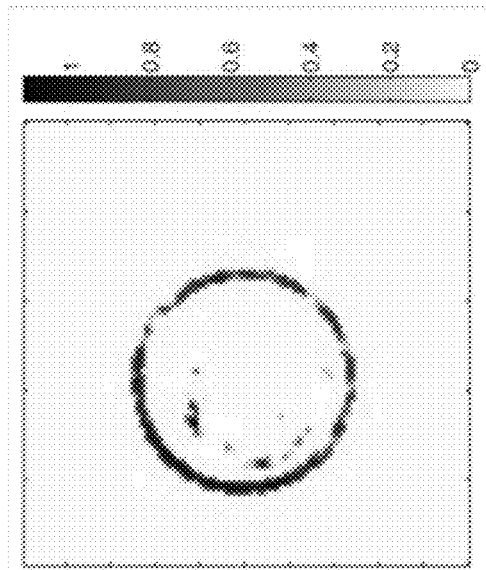
Figure 15C:
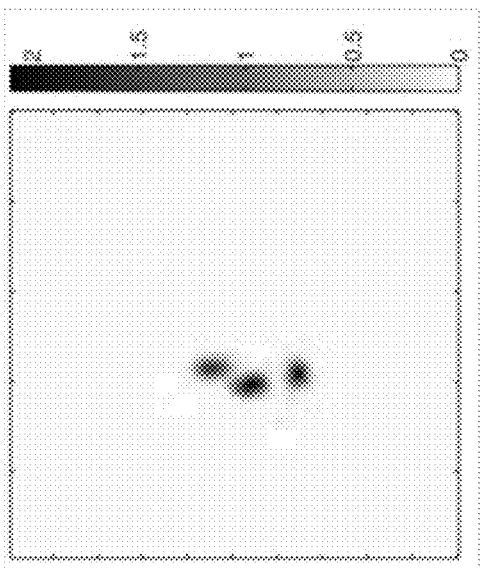
Figure 15D:
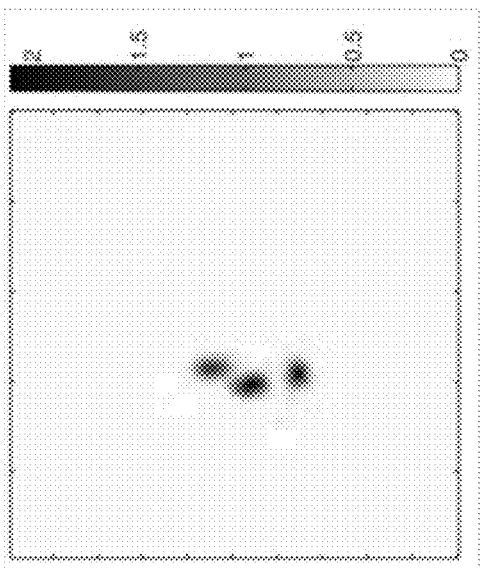

FIGS. 12A-12D show multiple views of volumetric reconstruction of carotid plaque specimen A taken from the 30-45 keV energy bin. For reference, a photograph of carotid plaque specimen A is shown in FIG. 12E in the same orientation as FIGS. 12A-12D. FIG. 13 shows transaxial slices of plaque specimen B from each of the five different energy levels.

The images were decomposed using the material+class method described herein; results are shown in FIGS. 14A-14D for specimen A, and FIGS. 15A-15D for specimen B. Classification images shown in FIGS. 14A and 15A were obtained using the simple difference classifier described herein. The material images shown in FIGS. 14B-D and 15B-D show quantitative estimates of material concentration in units of g/mL.

In general, the calcium-rich regions in the classification images were classified as calcium (FIGS. 14D and 15D); material concentrations were reasonable at 0.8-1.2 g/mL compared to the calcium chloride ex vivo samples queried in Example 3. The results also demonstrate some discrimination of adipose (FIGS. 14B, 15B), water (FIGS. 14C, 15C) and calcium (FIGS. 14D, 15D) components of the plaque specimens.

V. Conclusion

This disclosure is not intended to be exhaustive or to limit the present technology to the precise forms disclosed herein. Although specific embodiments are disclosed herein for illustrative purposes, various equivalent modifications are possible without deviating from the present technology, as those of ordinary skill in the relevant art will recognize. In some cases, well-known structures and functions have not been shown or described in detail to avoid unnecessarily obscuring the description of the embodiments of the present technology. Although steps of methods may be presented herein in a particular order, alternative embodiments may perform the steps in a different order. Similarly, certain aspects of the present technology disclosed in the context of particular embodiments can be combined or eliminated in other embodiments. While advantages associated with certain embodiments of the present technology may have been disclosed in the context of those embodiments, other embodiments can also exhibit such advantages, and not all embodiments need necessarily exhibit such advantages or other advantages disclosed herein to fall within the scope of the present technology. Accordingly, this disclosure and associated technology can encompass other embodiments not expressly shown or described herein.

Throughout this disclosure, the singular terms "a," "an," and "the" include plural referents unless the context clearly indicates otherwise. Similarly, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the terms "comprising" and the like are used throughout to mean including at least the recited feature(s) such that any greater number of the same feature and/or additional types of other features are not precluded. Directional terms, such as "upper," "lower," "front," "back," "vertical," and "horizontal," may be used herein to express and clarify the relationship between various elements. It should be understood that such terms do not denote absolute orientation. Reference herein to "one embodiment," "an embodiment," or similar formulations means that a particular feature, structure, operation, or characteristic described in connection with the embodiment can be included in at least one embodiment of the present technology. Thus, the appearances of such phrases or formulations herein are not necessarily all referring to the same embodiment. Furthermore, various particular features, structures, operations, or characteristics may be combined in any suitable manner in one or more embodiments.

I claim:

1. A device for characterizing atherosclerotic plaque, the device comprising:
a multi-energy x-ray source including at least three x-rays with different energies;
a detector configured to detect a plurality of x-rays emitted by the multi-energy x-ray source after passage through a blood vessel of a human subject including the atherosclerotic plaque, wherein the detector is further configured to (i) simultaneously count photons of at least three different energy levels, and (ii) generate aggregated spectral information corresponding to the detected plurality of x-rays; and
a computer operably coupled to the detector and configured to decompose the aggregated spectral information to identify and quantify one or more components of the atherosclerotic plaque, wherein decomposing the aggregated spectral information comprises:
constructing one or more images of linear attenuation for each of the at least three different energy levels at each location in the image, wherein each of the one or more images comprises a plurality of pixels;
decomposing each of the constructed images using a weighted least squares estimation; and
estimating a concentration of the one or more components in each pixel of each image of linear attenuation based on differences in measured linear attenuation coefficients for each of the at least three different energy levels.

2. The device of claim 1 wherein the multi-energy x-ray source includes five x-rays with different energies.

3. The device of claim 1 wherein the detector is configured to simultaneously count photons of at least five different energy thresholds.

4. The device of claim 1 wherein the detector is a cadmium-telluride detector.

5. The device of claim 1 wherein the multi-energy x-ray source and/or the detector is configured to rotate about the blood vessel containing the atherosclerotic plaque.

6. The device of claim 1 wherein the computer is configured to decompose the aggregated spectral information to identify and quantify one or more components of the atherosclerotic plaque.

7. The device of claim 1 wherein the detector is configured to count photons above 30 keV, above 45 keV, above 60 keV, above 80 keV, and above 100 keV.

8. The device of claim 1 wherein the computer is further configured to:
   construct an image of linear attenuation for each detected photon energy or band of energies, each image comprising a plurality of pixels;
   determine the presence of one or more components of the atherosclerotic plaque in each image of linear attenuation, wherein the one or more components is selected from a predetermined list of possible components likely to be present in the image;
   estimate a concentration of the one or more components in each image of linear attenuation; and
   display a map of at least one of the images of linear attenuation, the map including indicia of the concentration of the one or more components in the image of linear attenuation.

9. The device of claim 8 wherein determining the presence of one or more components of the atherosclerotic plaque in each image of linear attenuation comprises estimating a concentration of the one or more components in each pixel of each image of linear attenuation.

10. The device of claim 9, wherein the estimating comprises:
    performing a weighted least squares analysis of each pixel to provide a ratio of the one or more components associated with each pixel; and
    combining the ratio of the one or more components for all pixels.

11. The device of claim 10, wherein the weighted least squares analysis comprises weighting each detected energy range as a function based on a priori knowledge or based on the amount of x-ray photons detected in that range.

12. The device of claim 1 wherein the decomposing further comprises:
    decomposing, in an image domain, each of the constructed images into one or more materials; and
    predetermining a list of each of the materials at each location in the constructed images.

13. An x-ray computed tomography system, the system comprising:
    a polychromatic energy source, wherein the polychromatic energy source is a multi-energy x-ray source having including at least three x-rays with different energies;
    a detector configured to discriminate and count photons within at least three different energy bands;
    a platform disposed between the polychromatic energy source and the detector, the platform configured to temporarily secure atherosclerotic plaque at a predetermined distance from the polychromatic energy source; and
    a computer configured to receive the photon counts from the detector and generate at least one tomographic slice image of the atherosclerotic plaque, wherein the tomographic slice image includes information identifying and quantifying one or more components of the atherosclerotic plaque, wherein generating the information identifying and quantifying one or more components of the atherosclerotic plaque is generated by:
    constructing one or more images of linear attenuation for each of the at least three different energy bands at each location in the image, wherein each of the one or more images comprises a plurality of pixels;
    decomposing each of the constructed images using a weighted least squares estimation; and
    estimating a concentration of the one or more components in each pixel of each image of linear attenuation based on differences in measured linear attenuation coefficients for each of the at least three different energy bands.

14. The system of claim 13 wherein the polychromatic energy source and/or the detector is configured to move about the platform.

15. The system of claim 13 wherein the decomposing further comprises:
    decomposing, in an image domain, each of the constructed images into one or more materials; and
    predetermining a list of each of the materials at each location in the constructed images.

16. A method for identifying and quantifying one or more components of an atherosclerotic plaque in a subject, the method comprising:
    providing a device comprising:
    a multi-energy x-ray source including at least three x-rays with different energies,
    a detector configured to detect a plurality of x-rays emitted by the multi-energy x-ray source, to simultaneously count photons of different energy thresholds, and to generate spectral information corresponding to the detected plurality of x-rays, and
    a computer configured to decompose the spectral information to identify and quantify one or more components of the atherosclerotic plaque;
    positioning a subject having atherosclerotic plaque between the multi-energy x-ray source and the detector;
    applying x-ray energy comprising photons at a plurality of energy levels from the multi-energy x-ray source to the subject;
    detecting a plurality of photons having at least three x-rays with different energies with the detector;
    converting the detected photons into spectral information as a function of the at least three energy bands; and
    decomposing the spectral information to provide an identity and quantity of one or more components of the atherosclerotic plaque, wherein the decomposing comprises:
    constructing one or more images of linear attenuation for each of the at least three energy bands at each location in the image, wherein each of the one or more images comprises a plurality of pixel;
    decomposing each of the constructed images using a weighted least squares estimation; and
    estimating a concentration of the one or more components in each pixel of each image of linear attenuation based on differences in measured linear attenuation coefficients for each of the at least three energy bands.

17. The method of claim 16 wherein the identity and quantity of the one or more components of the atherosclerotic plaque is displayed tomographically.

18. The method of claim 16 wherein the detector simultaneously counts photons of at least five different energy thresholds.

19. The method of claim 16 wherein the estimating comprises:
   performing a weighted least squares analysis of each pixel to provide a ratio of the one or more components associated with each pixel; and
   combining the ratio of the one or more components for all pixels.

20. The method of claim 19 wherein the weighted least squares analysis comprises weighting each detected energy range as a function based on a priori knowledge or based on the amount of x-ray photons detected in that range.

21. The method of claim 16 wherein the decomposing further comprises:
   decomposing, in an image domain, each of the constructed images into one or more materials; and
   predetermining a list of each of the materials at each location in the constructed images.

* * * * *

UNITED STATES PATENT AND TRADEMARK OFFICE
CERTIFICATE OF CORRECTION

PATENT NO. : 9,538,971 B2
APPLICATION NO. : 14/313666
DATED : January 10, 2017
INVENTOR(S) : Adam Alessio It is certified that error appears in the above-identified patent and that said Letters Patent is hereby corrected as shown below:

On the Title Page

On the page 2, in Column 1, under "Other Publications", Line 16, delete "Recontruction" and insert -- Reconstruction --, therefor.

On the page 2, in Column 1, under "Other Publications", Line 23, delete "Assesment" and insert -- Assessment --, therefor.

In the Specification

In Column 8, Lines 51-54, delete "
$$\hat{\vec{a}}(\vec{x}) = \arg_{\vec{\alpha}}\min \sum_{e=1}^{E} \left[ \left( \hat{\mu}(e, \vec{x}) - \sum_{b=1}^{B} \alpha_b(\vec{x}) f_b(e) \right)^2 W_e \right]$$
" and insert --
$$\hat{\vec{a}}(\vec{x}) = arg_{\vec{\alpha}}min \sum_{e=1}^{E} \left[ \left( \hat{\mu}(e, \vec{x}) - \sum_{b=1}^{B} \alpha_b(\vec{x}) f_b(e) \right)^2 W_e \right]$$
--, therefor.

Signed and Sealed this
Twenty-eighth Day of November, 2017

Joseph Matal
*Performing the Functions and Duties of the*
*Under Secretary of Commerce for Intellectual Property and*
*Director of the United States Patent and Trademark Office*